| United States Patent [19] | [11] Patent Number: 4,977,252 |
|---|---|
| Chiu | [45] Date of Patent: Dec. 11, 1990 |

[54] MODIFIED STARCH EMULSIFIER CHARACTERIZED BY SHELF STABILITY

[75] Inventor: Chung-Wai Chiu, Westfield, N.J.

[73] Assignee: National Starch and Chemical Investment Holding Corporation, Wilmington, Del.

[21] Appl. No.: 234,070

[22] Filed: Aug. 18, 1988

Related U.S. Application Data

[63] Continuation-in-part of Ser. No. 167,051, Mar. 11, 1988, abandoned.

[51] Int. Cl.$^5$ ............... C08B 31/02; C08B 31/08; C08B 31/16
[52] U.S. Cl. ............................. 536/102; 536/112
[58] Field of Search ........................ 536/102, 111

[56] References Cited

U.S. PATENT DOCUMENTS

| 2,661,349 | 12/1953 | Caldwell et al. | 260/224 |
|---|---|---|---|
| 3,525,672 | 8/1970 | Wurzburg et al. | 195/31 |
| 4,035,235 | 7/1977 | Richards et al. | 195/31 |
| 4,428,972 | 1/1984 | Wurzburg et al. | 426/578 |
| 4,626,288 | 12/1986 | Trzasko et al. | 106/210 |

FOREIGN PATENT DOCUMENTS

0242913 10/1987 European Pat. Off. .

OTHER PUBLICATIONS

Trubiano, P., "Modified Starches: Properties and Uses", 1986, CRC Press, Boca Raton, Fla., Chap. 9, pp. 136–147.

Rutenberg, M. W., "Starch and Its Modifications" *Handbook of Water-Soluble Gums and Resins*, 1980, McGraw Hill, Inc., N.Y., N.Y., pp. 22–36.

*Encyclopedia of Chemical Technology*, Kirk-Othmer, Editor, 3rd Edition, Wiley-Interscience, N.Y., N.Y., 1979, vol. 8, pp. 900–910, 918, 923–925; vol. 12, pp. 55–56.

*Primary Examiner*—John Kight, III
*Assistant Examiner*—C. Azpuru
*Attorney, Agent, or Firm*—Mary E. Porter; Edwin M. Szala

[57] ABSTRACT

Modified starches useful for emulsifying industrial products, especially foods and beverages containing flavor oils, are prepared by enzymatic degradation of the 1,4-alpha-D-glucosidic linkages from the non-reducing ends of a starch molecule, preferably employing beta-amylase, which may be carried out before or after the preparation of a starch derivative containing a hydrophobic group or both hydrophilic and hydrophobic substituent groups. The enzymatic degradation provides a starch emulsifier whose emulsions are characterized by improved shelf stability, which emulsifier may be used as a replacement for gum arabic and in other industrial applications.

25 Claims, No Drawings

MODIFIED STARCH EMULSIFIER CHARACTERIZED BY SHELF STABILITY

This is a continuation-in-part of copending application Ser. No. 167,051 filed Mar. 11, 1988, now abandoned.

This invention relates to a modified starch that is useful in a shelf stable emulsion and as a replacement for gum arabic in systems requiring a stable oil-in-water emulsion, especially in beverages that are flavored with flavoring oils such as citrus oils. The invention also relates to a process for preparing the modified starch and to chemical compositions, food products, and beverages containing the modified starch.

BACKGROUND OF THE INVENTION

A variety of chemical compositions are used emulsifying agents in food, cosmetics, paint, pharmaceutical and polymer industries, as well as in textile and leather processing, ore flotation, oil drilling and agricultural spraying operations. In many of these applications, the emulsifying agent also functions as a stabilizer of the viscosity or fluidity of the continuous phase. Frequently, these applications require that the emulsion be shelf stable for long periods of time.

Typical compositions which function as water soluble emulsifiers and stabilizers include guar gum, gum arabic, and other gums, starches, proteins, various water soluble polymers, and the like. (See, *Encyclopedia of Chemical Technology,* Kirk-Othmer Editor, 3rd Edition, Wiley-Interscience, New York, N.Y., 1979, Vol. 8, pp. 900-910, 918, 923-25; Vol. 12, pp. 55-6.) Gum arabic is preferred in many applications for its shelf stability, particularly during refrigerated or frozen storage of the emulsion.

Gum arabic is a branched, substituted heteropolysaccharide characterized by extreme water solubility, low viscosity, and the absence of odor, color or flavor. Gum arabic has been used as an emulsifier and stabilizer in foods such as confections, syrups, flavor oil emulsions, ice cream and beverages, and in inks, adhesives, textiles and lithography solutions.

Gum arabic is a naturally occurring gum which is grown in the Middle East and Africa. Because gum arabic is obtained from these areas, it is expensive, and its supply and quality are unpredictable. Accordingly, industry has long searched for a shelf stable, low cost replacement for gum arabic, and starch derived products have been suggested for such use.

U.S. Pat. No. 2,661,349 issued Dec. 1, 1953 to Caldwell et al. discloses substituted dicarboxylic acid anhydride starch half ester derivatives. Certain of these derivatives form stable oil-in-water emulsions suitable for use in beverage emulsion, flavor emulsion, and other emulsion applications. (See, e.g., P. Trubiano, Chapter 9, in *Modified Starches: Properties and Uses,* CRC Press, Boca Raton, Fla., 1986, p. 134–47.) Cold water soluble, low viscosity octenylsuccinate starch derivatives have been successfully used to replace gum arabic in carbonated beverages. Higher viscosity octenylsuccinate derivatives have been useful as gum arabic replacers in salad dressings. Such substituted dicarboxylic acid starch half ester derivatives also have been used in place of gum arabic to encapsulate hydrophobic substances such as flavors, vitamins, fragrances and oils. The encapsulation is typically prepared by spray-drying an oil-in-water emulsion. Certain of these encapsulating agents have been modified to yield a composition which provides a gradual or controlled release of the entrapped flavor or oil. Others can be dissolved in water at higher solids than their gum arabic counterparts and may be superior to gum arabic in certain applications.

The low viscosity (converted) starches which are used in beverage and flavor emulsions are ordinarily prepared by acid degradation of the base starch. Processes for producing low viscosity starches are well-known. U.S. Pat. No. 4,035,235 issued July 12, 1977 to Richards et al. discloses a method for degradation of lipophilic substituted starches which uses alpha-amylase digestion as an alternative to acid degradation for preparing low viscosity starches. The lipophilic substituted starches are suitable for flavor encapsulation and oil-in-water emulsions. These conversion methods produce starch products which are suitable as emulsifiers and encapsulating agents for oils used in beverages.

One drawback to the use of the known starch derived products in replacing gum arabic is that known starch derivatives are less stable during storage. These starch derivatives display shorter shelf-life and poorer refrigeration and freeze/thaw stability than gum arabic. Therefore, in certain applications, such as flavored syrup bases used in the manufacture of soft drinks and similar types of beverages, these starch derived substitutes do not perform as well as gum arabic. Because beverage manufacturers ship flavored syrup bases to bottlers in diverse locations where the syrup bases may be held in refrigerated storage for long periods of time prior to use in the bottling operation, the flavor oil emulsion must remain stable during storage. In addition, because refrigeration temperatures may vary from bottler to bottler, or from day to day, the flavor oil emulsion must be able to withstand temperature cycling, including freeze/thaw cycles.

The stability problem in beverage applications is thought to occur because of the tendency of starch products to retrograde, causing the flavor oil emulsion to break down upon temperature cycling or long term storage. In severe cases, the starch may retrograde to form a gel and the flavor oil may separate entirely from the water phase. Retrogradation of starches is essentially a crystallization process that occurs when linear portions of the starch molecules align themselves next to each other and form interchain hydrogen bonds through the hydroxyl groups. When sufficient interchain bonding occurs, the molecules associate to form molecular aggregates which display a reduced capacity for hydration and, therefore, lower water solubility. These aggregates may precipitate, or, in more concentrated solutions, may form a gel. The tendency to retrograde is more pronounced in starches containing high levels of the linear amylose molecule. In starches containing both linear (amylose) and branched (amylopectin), or only branched molecules, the tendency to retrograde is less pronounced. As the temperature is lowered, both amylose and amylopectin containing starches display a greater tendency to retrograde.

Retrogradation has been partially overcome in certain applications by chemically derivatizing the starch molecule to stabilize the starch by interfering with the association between starch molecules, or portions of the same molecule, and thereby reducing the tendency of the starch to lose its hydration ability on storage. For example, reacting the starch with a reagent to introduce substituents such as hydroxypropyl, phosphate, acetate or succinate groups tends to stabilize the starch molecule during storage. These derivatization reactions may be carried out on starches which are further modified by crosslinking or degradation to obtain starches for particular applications. However, these derivatized starches do not provide the stable emulsification properties which are typical of gum arabic.

Other processes known to limit starch retrogradation at low temperatures also do not provide stable emulsifying starches. For example, U.S. Pat. No. 3,525,672 issued Aug. 25, 1970 to Wurzburg et al., discloses treating a crosslinked, inhibited starch thickener with an enzyme such as beta-amylase to impart freeze/thaw stability to starch thickeners for pie fillings, puddings and other thickened foods which are subjected to low temperature storage. It is stated that in addition to the described inhibition procedure, it is sometimes advantageous to partially derivatize the starch bases. Typical substituent groups include ester groups such as acetate, succinate, phosphate and sulfate groups as well as ether groups.

U.S. Pat. No. 4,428,972 issued Jan. 31, 1984 to Wurzburg et al., discloses a waxy starch thickener with superior low temperature stability in aqueous dispersions, which starch is obtained from a selected plant of a $wxsu_2$ genotype.

However, none of these inventions for overcoming retrogradation during low temperature storage disclose a starch product useful for preparing a shelf stable oil-in-water emulsion. Thus, there remains a need for a product which combines the properties of emulsification with stability during shelf storage, refrigeration and freeze/thaw cycles, and which may be used to replace gum arabic.

Accordingly, it is an object of the present invention to provide an improved modified starch which exhibits the stable emulsification characteristics of gum arabic. It is a further object to provide a method for producing such a modified starch.

It is a further object to provide products containing starch based emulsions having good shelf stability, particularly foods and beverages containing flavor oil emulsions.

SUMMARY OF THE INVENTION

This invention relates to a process for enzyme degradation of an emulsifying starch, which starch provides emulsions with improved shelf stability. This invention also relates to a modified starch product from the enzyme degradation process. It also provides industrial products, especially foods and beverages containing flavor oil emulsions, and encapsulated flavor oils that are prepared from the starch based product.

The enzyme treatment utilized in the process of this invention is carried out on starches after they have been derivatized to contain either hydrophobic groups, or groups comprising both hydrophilic and hydrophobic moieties, so as to have emulsifying properties. Alternatively, the enzyme treatment is carried out before the starch derivative has been prepared. Methods for preparing such derivatives are disclosed in U.S. Pat. No. 2,661,349 mentioned earlier and incorporated herein by reference. The preferred starch base is a starch alkenyl succinate half ester, wherein the carboxyl group may be present as an acid or a carboxylate salt. It is noted, however, that any method which yields the desired hydrophobic function or a blend of hydrophobic and hydrophilic functions on the starch molecule, and thereby provides it with emulsifying properties, can be used to prepare the modified starch herein. Suitable derivatives and methods for producing them are disclosed in U.S. Pat. No. 4,626,288 issued Dec. 2, 1986 to Trzasko, et al. and incorporated herein by reference. The treatment with an exo-enzyme capable of cleaving the 1, 4-alpha-D-glucosidic linkages from the non-reducing end of the starch molecule but incapable of cleaving the 1, 6-alpha-D-glucosidic linkages of the starch molecule, is carried out until up to 70% (preferably up to 55%), by weight, of the starch derivative containing a hydrophobic group or both a hydrophilic group and a hydrophobic group has been degraded to maltose.

In preparing the modified degraded starch of the invention, the desired starch base is slurried in water in any proportion needed to achieve the desired enzyme-substrate concentration or calculated to suit the end use. The mixture is then cooked to gelatinize the starch. If desired, the starch may be used in the granular form, but enzymatic degradation of granular starch proceeds slowly. The temperature and pH of the mixture are then adjusted to the optimums recommended by the manufacturer or supplier for the particular enzyme to be used in preparing the starch product.

The enzyme must be an exo-enzyme, capable of cleaving the 1,4-alpha-D-glucosidic linkages from the non-reducing end of the starch molecule, and incapable of cleaving the 1,6-alpha-D-glucosidic linkages. Beta-amylase, which is preferred, is a very specific exo-enzyme which, by its action, is able to form a reaction complex only from the non-reducing ends of the starch molecule with a maltoside group which is linked to a glucose group via a 1,4 alpha-D-glucosidic linkage. Thus, the enzyme attacks starch only at the non-aldehydic end (the non-reducing end) thereby splitting off maltose units from these outer branches until a point of branching (a 1,6 linkage) is reached. A single maltose or glucose unit remains at each branch point of the starch molecule after enzyme treatment. Since this exoenzyme is capable of splitting the 1,4 linkages of the starch molecule but is not capable of splitting the 1,6 linkages, the residue of such a degradation procedure is a compact molecular structure which is substantially free of outer branches or contains only short outer branches. This product is thus devoid of long outer chains which cause the retrogradation and syneresis evident in aqueous starch dispersions which have been exposed to long periods of storage and/or repeated freeze/thaw cycles.

The enzyme is permitted to digest the starch base until up to 70% (preferably up to 55%), by weight, of the starch has been degraded to maltose, or until the desired end point (i.e., sufficient degradation to provide improved shelf stability of a particular emulsion prepared with the starch) has been reached. The end point may be determined by change in viscosity, by reducing sugar content, or by any other method known in the art for measuring the level of enzyme degradation of the starch molecule. In the alternative, the enzyme degradation may continue until substantially all of the available maltose units have been removed from the starch molecule Ordinarily the degradation will be carried out for periods ranging from a few hours to 24 hours or more depending on the temperature, enzyme and substrate concentrations, and other variables. The enzyme degradation is then terminated by means of heat, chemical additions, or other methods known in the art for deactivating an enzyme or separating an enzyme from its substrate.

The resulting degraded starch composition may be spray-dried, drum-dried or otherwise recovered in a form suitable for the intended application.

It is to be understood that the invention herein includes any emulsified composition wherein the emulsifying agent is starch which has been enzymatically modified to improve shelf stability of an emulsion. Thus, it is meant to include emulsions comprising a blend of the modified starch and gums or other emulsifying agents.

The modified starches of the invention may be advantageously employed in any product wherein gum arabic has been used as an emulsifier, stabilizer, or the like, and in any product where high molecular weight, water soluble emulsifiers have been used to form or stabilize emulsions. Thus, it may be used in beverages that are flavored with oils such as orange or lemon oils, confectionery items, ice cream, other beverages and other food products which require a shelf stable emulsifier. It may be used in water-and-alcohol based beverages. The starches also may be used in preparing spray-dried flavor oils which are reconstitutable with water to provide flavor emulsions, and in inks, textiles and other non-food end uses.

DESCRIPTION OF THE PREFERRED EMBODIMENTS

The applicable starch bases which may be used in preparing the enzyme degraded starch herein may be derived from any plant source including corn, potato, sweet potato, wheat, rice, sago, tapioca, waxy maize, sorghum, and the like. Also included are the conversion products derived from any of the above bases including, for example, fluidity or thin-boiling starches prepared by oxidation, alpha-amylase conversion, mild acid hydrolysis or heat dextrinization, and derivatized starches such as ethers and esters.

The starch base will preferably be a gelatinized starch (a precooked, non-granular starch) and also may be a fluidity starch converted by mild acid degradation, or heat dextrinization methods that are well known in the art. (See e.g., M. W. Rutenberg, "Starch and Its Modifications" in *Handbook of Water-Soluble Gums and Resins*, R. L. Davidson, editor, McGraw Hill, Inc., New York, N.Y., 1980, pp. 22–36.) A combination of one or more of these conversion techniques may be used. The conversion is typically carried out before treatment with the hydrophobic/hydrophilic (or merely hydrophobic) reagent and before the beta-amylase treatment. If desired, the starch base may be converted by treatment with an alpha-amylase enzyme to produce a fluidity starch in the manner disclosed in U.S. Pat. No. 4,035,235. Conversion with alpha-amylase also is typically carried out before beta-amylase treatment. Where a high viscosity emulsification system is desired, it is not necessary to convert the base starch.

The starch may be derivatized by treatment with any reagent which contributes emulsification properties to the starch. The derivatization may be carried out before or after beta-amylase treatment. The reagent must contain a hydrophobic moiety and may contain a hydrophilic moiety. The hydrophobic moiety should be an alkyl, alkenyl, aralkyl or aralkenyl group which contains at least five carbon atoms, and preferably five to twenty-four carbon atoms. As in the preferred embodiment set forth below, the hydrophilic moiety may be contributed by the reagent, or, as in other embodiments, the starch's own hydroxyl groups serve as the hydrophilic moiety and the reagent only contributes a hydrophobic moiety.

In a preferred embodiment, the starch is derivatized by reaction with an alkenyl cyclic dicarboxylic acid anhydride by the method taught in U.S. Pat. No. 2,661,349. However, any process for derivatizing starch which yields the desired blend of hydrophobic and hydrophilic functions on the starch molecule, and thereby yields stable emulsification properties, may be used to prepare the modified starch claimed herein. This includes processes not now known in the art.

Where a low viscosity emulsifier is desirable, the preferred embodiment is an octenylsuccinate half ester derivative of an amylopectin containing starch, such as waxy maize, which has been converted to a Water Fluidity (WF) of up to about 60. Water Fluidity is an empirical test of viscosity measured on a scale of 0–90 wherein fluidity is the reciprocal of viscosity. Water Fluidity of starches is typically measured using a Thomas Rotational Shear-Type Viscometer (manufactured by Arthur H. Thomas Co., Philadelphia, Pa. 19106), standardized at 30° C. with a standard oil having a viscosity of 24.73 cps., which oil requires $23.12 \pm 0.05$ sec. for 100 revolutions. Accurate and reproducible measurements of the Water Fluidity are obtained by determining the time which elapses for 100 revolutions at different solids levels depending on the starch's degree of conversion (as conversion increases, the viscosity decreases). In a preferred embodiment, the converted starch is treated with at least 0.25%, and preferably 3.0% of the octenylsuccinic acid anhydride. If desired, a hydroxypropyl octenylsuccinate derivative may be used.

For other products, any degree of substitution or level of conversion that results in the desired viscosity and emulsification characteristics may be employed. For example, U.S. Pat. No. 4,035,235 discloses a suitable embodiment, comprising a method for producing a lipophilic derivative of starch to be used as an alternative to gum arabic in encapsulating water insoluble substances, such as volatile flavoring oils and perfumes.

In a preferred embodiment, the next step after preparing the starch derivative is to gelatinize the derivatized starch. The gelatinization process unfolds the starch molecules from the granular structure, thereby permitting the enzyme to more easily and uniformly degrade the outer branches of the starch molecules. After a slurry of the starch base has been gelatinized, the solids, temperature and pH of the slurry are adjusted to provide optimum enzyme activity.

The optimum parameters for enzyme activity will vary depending upon the enzyme used. Thus, the rate of enzyme degradation depends on factors including the type of enzyme used, enzyme concentration, substrate concentration, pH, temperature, the presence or absence of inhibitors and other factors. Depending on the type of enzyme, or its source, various parameters may require adjustment to achieve optimum digestion rate. In general, the preferred enzyme digestion reaction is carried out at the highest solids content that is feasible to facilitate subsequent drying of the starch composition while maintaining optimum reaction rates. For example, for the barley beta-amylase used herein to produce an emulsifier for beverage applications, a precooked starch dispersion at a solids content ranging up to 33% is preferred. Higher solids may be used, however, at higher solids agitation is difficult or ineffective and the starch dispersion is more difficult to handle.

Although the process of this invention is illustrated employing beta-amylase as the enzyme component, other enzymes, such as exo-alpha-1,4-glucosidase, exo-1,4-alpha-D-glucan maltotetrahydrolase, exo-1,4-alpha-D-glucan maltohexahydrolase, or any other exo-enzyme which exhibits selectivity in cleaving the 1,4-linkages of the starch molecule from the non-reducing ends, but leaving the 1,6-linkages intact, may be used to prepare the modified starch herein.

Because such exo-enzymes remove glucose, maltose, or larger saccharide units only from the outer branches of the amylopectin molecule, and do not debranch the molecule, the enzymatic degradation process yields molecules in which the short chain branch points remain intact. In amylopectin, branch points occur at approximately four to five percent of the monosaccharide units of the molecule. Following enzymatic degradation of amylopectin, the outer branches of the molecule are shortened to the point where association with other branches is reduced or eliminated, and the remaining 1,6 branch points prevent the inner branches from associating. Therefore, degraded molecules show improved resistance to retrogradation during storage and during freeze/thaw cycles. It is for this reason that an exoenzyme capable of cleaving the 1,4, but not the 1,6, linkages from the non-reducing ends of the starch molecule is a necessary element of the invention herein.

Although the process of this invention makes use of an enzyme in solution, processes utilizing an enzyme immobilized on a solid support are intended to fall within the scope of this invention.

Optimum concentrations of enzyme and substrate are governed by the level of enzyme activity. Enzyme activity may be expressed in Degrees of Diastatic Power (DP°) per ml of aqueous enzyme solution. The DP° is the amount of enzyme, contained in 0.1 ml of a 5% solution of the sample enzyme preparation, that will produce sufficient reducing sugars to reduce 5 ml of Fehling's solution when the sample is incubated with 100 ml of substrate for one hour at 20° C. The procedure for determining DP° is published in the *Food Chemicals Codex*, Third Edition, National Academy Press, Washington, D.C., 1981, p. 484.

A DP° in excess of 334 per 100 g of starch on a dry weight basis is needed to degrade gelatinized starch solutions containing up to 33% solids within 8 hours under optimum conditions of temperature and pH. A DP° of 840-1,110 per 100 g of starch on a dry weight basis (at a pH of 5.3 and temperature of 57° C.) is preferred.

The reaction may proceed in the presence of buffers to ensure that the pH will be at the optimum level throughout the degradation. Buffers such as acetates, citrates, or the salts of other weak acids are acceptable. Other agents may be used to optimize enzyme activity. The reaction may be carried out in a pH range from about 3-10, with the preferred range being between 5 and 7, and the optimum being 5.7 at 55°-60° C.

The aqueous starch dispersion should be held during the enzymatic digestion at a temperature of about 20°-100° C., the preferred range being 55°-60° C. and the optimum being 57° C. However, if shorter reaction times are desired, a temperature range from 60°-63° C. or a higher enzyme concentration may be used. As with other parameters of the enzyme reaction, the preferred and optimum temperature ranges will vary with changes in other parameters such as substrate concentration, pH and other factors affecting enzyme activity, and can be determined by the practitioner.

The enzyme reaction is permitted to continue until the desired level of degradation is reached or until substantially all of the available maltose has been removed from the starch molecule. The progress of enzyme reaction may be measured by various methods. If all critical parameters have been established for achieving a particular starch composition, then the reaction may be allowed to proceed to a predetermined relative end point in time (i.e., 8 hours in Example I). The end point also may be monitored and defined by measuring the concentration of reducing sugars. The maltose which is produced by 1,4-alpha-D-glucosidase activity is a reducing sugar which is easily measured by methods well known in the art. Other techniques such as monitoring the change in viscosity or the change in molecular weight may be used to define the reaction end point.

In a preferred embodiment, the degradation end point is measured by determining the percent reducing sugars contained in the reaction medium. Each maltose unit contains two glucose units but only one reducing group that can be detected in a reducing sugar assay. Therefore, the percentage, by weight, of reducing sugars (calculated as glucose) is approximately equal to one-half of the percentage, by weight, of maltose units formed by degradation of the starch molecule. If the beta-amylase is contaminated with high levels of alpha-amylase, then the reaction medium may contain even higher levels of reducing groups, and reducing sugar measurements must be standardized to take into account the effect of such contamination on the measurement of the progress of the enzyme reaction. In the alternative, the maltose may be measured directly by other types of analyses known in the art.

The degree of starch degradation that is required to substantially improve the low temperature stability of the starch composition is subject to variation. It depends on the type of starch utilized, the presence and nature of any substituent groups and the degree, if any, of conversion. Starch degradation ranging from 13-55%, by weight, is known to yield improved low temperature stability in thickeners. (See U.S. Pat. No. 3,525,672.) For low viscosity emulsification applications (i.e., starches converted to a WF of 40-60), degradation progresses until up to 70%, by weight, of the starch, as measured by reducing sugar content of the starch dispersion, has been hydrolyzed to maltose.

The maximum amount of enzymatic degradation to maltose which can be theoretically achieved employing pure betaamylase and unconverted starch is about 55%, by weight, of the starch. Pure beta-amylase is not readily available on a commercial basis. The beta-amylase which is commercially available contains small amounts of alpha-amylase, an endoenzyme which cleaves internal starch branches at random, freeing these branches for beta-amylase activity. Starch conversion by acid, heat or oxidation, has a similar, but less pronounced effect on beta-amylase degradation of starch. Thus, degradation of up to 70%, by weight, of the starch may be achieved employing commercially available beta-amylase which is contaminated with small amounts of alpha-amylase.

After the desired degree of starch degradation has been reached, the enzyme may be deactivated. Beta-amylase is rapidly deactivated at temperatures of about 100° C., therefore, the reaction may be conveniently terminated by increasing the temperature of the starch dispersion to at least 75° C. for at least 15 minutes.

The practitioner will recognize that the sequence of steps in the process of this invention may be carried out in any order, and are not limited to the preferred embodiment set forth above. Thus, in a second preferred embodiment, the sequence is reversed so that the enzymatic degradation step is completed prior to the derivatization step.

If the end-use application requires purification of the starch composition, the maltose and other reaction impurities and by-products may be removed by dialysis, filtration, centrifugation or any other method known in the art for isolating and concentrating starch compositions.

If a dried starch composition is desired for end use applications, the starch composition may be dehydrated by any method known in the art.

In beverage flavor emulsion applications waxy maize starches, converted to a Water Fluidity of about 40-60, are preferred.

For low viscosity emulsifiers, the reduction in viscosity during enzyme reaction may be used for determining when the desired level of degradation has been reached. A method for monitoring the viscosity of the reaction solution is described herein in Example I. Any of the many methods known in the art for measuring viscosity may be used. However, viscosity may be altered by factors other than the desired enzyme activity. For example, if the beta-amylase contains large amounts of alpha-amylase, then reduction in viscosity cannot be directly correlated to beta-amylase activity. Therefore, the level of alpha-amylase contamination must be carefully monitored and controlled if viscosity changes are used to determine the level of enzyme degradation. If the beta-amylase, or any other 1,4-alpha-D-glucosidase used herein, contains high levels of alpha-amylase contaminant, then the beta-amylase may be purified prior to use, or an alpha-amylase inhibitor may be added to the reaction dispersion.

The following examples will more fully illustrate the embodiments of this invention. In these examples, all parts and percentages are given by dry weight basis and all temperatures are in degrees Celsius unless otherwise noted. Shelf stability is measured at low temperature to accelerate retrogradation and shorten the testing period.

EXAMPLE 1

This example illustrates the preparation of a modified starch of the invention for use in beverage flavor emulsification.

An octenylsuccinate derivative (OSA) of waxy maize starch was prepared by the method disclosed in Example II of U.S. Pat. No. 2,661,349 except that the corn starch was replaced by waxy maize. In addition, the starch was reacted with 3% octenylsuccinic acid anhydride, rather than with 0.5% as disclosed in the reference. A 28% aqueous slurry of the OSA waxy maize was jet cooked at approximately 300° F. (149° C.). Thereafter, the cooked OSA waxy maize was placed in a constant temperature bath and maintained at 55°-60° C. with constant stirring. The pH was adjusted to 5.3 with 3% hydrochloric acid.

The cooked OSA waxy maize dispersion was divided into four batches and a different level of barley beta-amylase (1,4-alpha-D-glucan maltohydrolase (E.C. 3.2.1.2), obtained from Fermco Biochemics, Inc., Elk Grove Village, Ill.) was added to each batch. The amounts of enzyme added were 168, 334, 840 and 1,110 DP° per 100 g dry basis of OSA waxy maize. It had been determined in previous experiments that this relative range of enzyme concentration would produce the desired starch degradation in approximately eight hours. The three batches which contained at least 334 DP degrees per 100 g of starch reached the desired degree of degradation in 3-8 hours.

The degree of degradation was determined by monitoring the funnel viscosity of the dispersion. Accordingly, the level of alpha-amylase contamination present in the barley beta-amylase was monitored and limited to no more than 0.4 DU/ml of enzyme solution so that the viscosity would not be affected by this variable. A DU (Dextrinizing Unit) is the quantity of alpha-amylase that will dextrinize soluble starch, in the presence of an excess of beta-amylase, at the rate of 1 gm/hour at 20° C.

To measure funnel viscosity, 38 g of the converted starch (anhydrous basis) was weighed into a tared 250 ml beaker (stainless steel) containing a thermometer and brought to 200 g total weight with distilled water. The sample was mixed to dissolve any lumps and heated or cooled to 72° F. (22° C.) A total of 100 ml of the cooked starch dispersion was measured into a graduated cylinder. It was then poured into a calibrated funnel while using a finger to close the orifice. A small amount was allowed to flow into the graduate to remove any trapped air, and the complete balance remaining in the graduate was poured back into the funnel. Using a timer, the time required for the 100 ml sample to flow through the apex of the funnel was recorded.

The funnel was a standard 58°, thick-wall, resistance glass funnel whose top diameter was about 9-10 cm with the inside diameter of the stem being about 0.381 cm. The funnel was calibrated so as to allow 100 ml of water to go through in 6 seconds using the above procedure.

By carefully controlling the parameters of the funnel viscosity test and limiting alpha-amylase contamination, the degree of starch degradation by beta-amylase was correlated to the loss in viscosity. The reducing sugars were measured by the Fehling method to confirm the degree of degradation.

In this example, the desired enzyme reaction end point was reached within a funnel viscosity range from 9-50 seconds. The reducing sugars content of these samples ranged from 29-35%. The corresponding degradation of the starch, by weight, ranged from 58-70%. When the targeted viscosity was reached, the enzyme was deactivated by injection of live steam into the reaction solution until a temperature of at least 75° C. was attained and held for at least 15 min. The batches were then spray-dried at an inlet temperature of 200°-210° C. and an outlet temperature of 85°-90° C. using a standard #22 1¼ J nozzle obtained from Spraying Systems Company. The spray-dried starch product was screened through #40 mesh screen.

EXAMPLE II

This example illustrates that aqueous dispersions of the product produced in Example I are stable through numerous freeze/thaw cycles, and, by extrapolation, are stable through prolonged storage. This example also illustrates that the beta-amylase-degraded starches of the invention are more stable at low temperature than the control starch which is not beta-amylase-degraded.

Using the methods set forth in Example I, OSA waxy maize and acid degraded 50 WF OSA waxy maize were degraded with beta-amylase. Together with a control consisting of an acid-converted OSA waxy maize which is presently used in beverage flavor emulsions, the beta-amylase degraded starches were dispersed in water at 20% solids and placed in a freezer. In one set of tests, the dispersions were subjected to 6 freeze/thaw cycles, in which the freeze portion of the cycle ranged from 1 to 5 days in duration, over a 22 day period. In another set of tests, dispersions were subjected to a series of 6 freeze/thaw cycles, in which the freeze portion of the cycle ranged from 1 to 5 days in duration, over an 18 day period. After each freeze/thaw cycle, viscosities were measured with a Brookfield viscometer at ambient temperature [about 72° F. (22° C.)] with a #3 spindle at 10 rpms.

The viscosity of the control increased, a visible floc formed, and then the viscosity decreased. The viscosities of the enzyme treated samples showed little variation other than the variation inherent in Brookfield viscometer readings at low viscosity. In addition, the floc which formed in the control after one freeze/thaw cycle, was absent from the enzyme-treated samples even after 6 freeze/thaw cycles. Thus, the enzyme-degraded starch compositions show a greater resistance to retrogradation during temperature cycling and, by extrapolation, during shelf storage than the control composition which is presently used to replace gum arabic in beverages.

EXAMPLE III

This example illustrates that the modified starch which has been purified by removal of the beta-amylase freed maltose remains resistant to retrogradation during storage.

Beta-amylase degraded OSA waxy maize prepared by the method set forth in Example I above was subjected to dialysis to remove maltose. The starch was dispersed in distilled water at 15-20% solids and placed in a dialysis tube (obtained from Spectropor Membrane) that retained molecules with molecular weights in excess of 6,000-8,000. The dispersion was dialyzed against distilled water until the dialyzate was free of all organic materials. The starch was then collected by precipitation with ethanol.

Along with a maltose-containing sample prepared as in Example I, the maltose-free sample was refrigerated at 5°-7° C. over a period of 83 days. Samples were periodically removed and subjected to differential scanning calorimetry (DSC) analysis to determine the minimum number of days required for the sample to retrograde. The DSC analysis was conducted by the method reported by A. C. Eliasson in "Retrogradation of starch as measured by differential scanning calorimetry", *Prog. Biotechnol,* 1:93-8 (1985).

The maltose-free sample showed no retrogradation even after storage for 83 days under refrigeration. Thus, like the maltose-containing beta-amylase degraded starches, the maltose-free starch displays increased resistance to retrogradation relative to a currently used OSA waxy maize emulsifier. (See Table I.) Therefore, the presence of maltose is not essential to improving stability of the degraded starch.

TABLE I

| Starch | Number of Days to DSC* Detectable Retrogradation of 50% Starch Dispersions |
|---|---|
| Beta-amylase-Degraded OSA Derivative of Waxy Maize | >83 Days |
| Beta-amylase-Degraded OSA Derivative of Acid Converted Waxy Maize | >83 Days |
| Beta-amylase-Degraded Myristate Ester Derivative of Acid-Converted Waxy Maize | >83 Days |
| Maltose Free Beta-amylase-Degraded OSA Derivative of Waxy Maize | >83 Days |
| Control: OSA Derivative of Waxy Maize | 4 Days |
| Control: OSA Derivative of Alpha-amylase-Converted Waxy Maize | 14 Days |
| Control: OSA Derivative of Acid-Converted Waxy Maize | 4 Days |
| Control: Myristate Ester Derivative of Acid-Converted Waxy Maize | <1 Day |

*Differential Scanning Calorimeter

EXAMPLE IV

This example illustrates that the beta-amylase-degraded starch displays improved resistance to retrogradation during storage.

Aqueous dispersions at 50% solids were prepared with the following starches:

(1) beta-amylase-degraded OSA waxy maize, (from Example I, above)

(2) beta-amylase-degraded, 50 WF acid converted OSA waxy maize, (from Example II, above)

(3) beta-amylase degraded, 50 WF acid-converted, myristate ester of waxy maize, prepared by the method set forth below, (4) 50 WF acid-converted, myristrate ester of waxy maize control, prepared by the method set forth below, (5) alpha-amylase-converted OSA waxy maize control, (6) acid-converted OSA waxy maize control, and (7) OSA waxy maize control.

All beta-amylase-degraded samples were prepared by the method set forth in Example I. All OSA samples were prepared by the method set forth in Example I. The myristate ester samples were prepared by slurrying 200 g of 50 WF acid-converted waxy maize starch in 300 ml of water, adjusting the pH to 8.0 by the addition of 3% NaOH, and adding 20 g of N-myristyl-N-methylimidazolium chloride over 10 to 15 minutes. The reaction continued for 2 hours and additional water was added to facilitate stirring when the reaction mixture thickened. The reaction mixture was filtered, the starch was resuspended, the pH was adjusted to 5.5, and then filtered, washed with methanol and dried. The starch product contained about 5% myristate ester by weight.

Along with the controls and the maltose-free sample of Example III, above, these starch dispersions were subjected to storage under refrigeration at 5°-7° C. Periodically, samples were evaluated for retrogradation by the DSC analysis method set forth in Example III.

Table I summarizes the number of days needed for each starch composition to retrograde to a point detectable by DSC analysis.

The results show that the controls which were not treated with beta-amylase rapidly retrograded, while the treated samples did not retrograde to a point detectable by DSC analysis throughout the 83 days during which the study was conducted.

EXAMPLE V

This example illustrates that a variety of starches and starch derivatives will exhibit improved shelf stability and, in certain cases, improved ability to form an emulsion, following beta-amylase degradation.

A group of starches, including acid-converted tapioca with a funnel viscosity of 33.6 seconds at 19% solids and 72° F. (2220 C.), 40 WF fluidity corn and a hydroxypropyl 84 WF acid-converted waxy maize derivative, were reacted with octenylsuccinic acid anhydride to form the OSA derivative by the method set forth in Example I. A 5% myristate ester derivative of 50 WF waxy maize was prepared by the method set forth in Example IV. A blend of sixteen to twenty-four carbon atom hydrocarbon chain ethers of waxy maize starch was prepared by mixing 100 g of the starch with 3 g of 3-Chloro-2-hydroxypropyl-cocoalkyl dimethylammonium chloride (Quab 360 [$C_{16-24}$ $H_{25-33}$ NO $Cl_2$], obtained from Degussa Co.) at pH 11.5–12. The starch mixture was heated to 40° C., permitted to react for 16 hours, and then was neutralized to pH 5.5–6, washed three times with water and dried. This starch ether derivative was subjected to beta-amylase degradation in the manner set forth in Example I, (with one exception) and spray-dried. The exception was that the beta-amylase degradation was terminated when the funnel viscosity of the reaction medium reached that of a control blend of sixteen to twenty-four carbon atom hydrocarbon chain ether of 50 WF waxy maize starch. The control starch ether was prepared by the method set forth above, except that the starting material was an acid-converted 50 WF waxy maize starch.

All other samples of each starch derivative were subjected to enzyme degradation in the manner set forth in Example I and spray-dried.

Samples of the spray-dried starch derivatives (20 g) were mixed with 180 gm of distilled water. This dispersion was agitated in a Waring blender at low speed with a powerstat setting of 25–30 for 2 minutes. A citrus oil blend (80 g) was added to the center of the vortex at slow speed. The citrus oil blend was a mixture of 12 parts of single fold orange oil obtained from Fritzsche-Dodge-Olcott and 3.4 parts of Ester Gum #8 BE obtained from Hercules Company. The starch dispersion and oil were emulsified for 2 minutes at high speed in a Waring blender. The resulting emulsions were placed in a glass jar, capped, placed in a freezer, and periodically removed and warmed to room temperature. The evaluation consisted of visually examining the emulsification for separation, oiling and gelling. All samples, except those which did not form stable emulsions at room temperature, were also evaluated after refrigerated storage.

The control 40 WF acid-converted OSA corn starch gelled at room temperature and did not form an emulsion. The control hydroxypropyl 84 WF acid-converted waxy maize and the control myristate ester of 50 WF acid-converted waxy maize formed emulsions which separated immediately at room temperature. Similarly, the control acid-converted tapioca did not form an emulsion. The control ether of 50 WF acid converted waxy maize formed a poor emulsion which displayed pale-yellow creaming at room temperature and oiled out after refrigeration for 1 day.

In contrast, the beta-amylase degraded 40 WF acid-converted OSA corn starch formed an emulsion which separated only after two freeze/thaw cycles and the beta-amylase degraded acid-converted OSA tapioca starch formed an emulsion which separated after one freeze/thaw cycle. The beta-amylase degraded hydroxypropyl-OSA was stable through seven freeze/thaw cycles The beta-amylase degraded 5% myristate ester of waxy maize formed an emulsion that was stable through the single freeze/thaw cycle tested and after three weeks of refrigerated storage. The beta-amylase degraded ether of waxy maize formed an emulsion which was stable at room temperature and remained stable after two freeze/thaw cycles over a twelve day period. All other beta-amylase treated samples formed emulsions which were stable after six months of refrigerated storage. In all instances, the beta-amylase degraded samples performed better than their respective controls.

The results show that beta-amylase degradation of OSA starches, such as waxy maize, corn and tapioca derivatives, will improve the shelf stability of oil-in-water emulsions formed with these starches. The results are the same regardless of whether the starch is derivatized with a hydrophobic/hydrophilic substituent, such as OSA, or with a merely hydrophobic substitutent, such as myristate. In addition, the results illustrate that where the particular application calls for a derivative such as a hydroxypropyl OSA waxy maize, enzyme degradation of such a derivative will yield a low temperature stable oil-in-water emulsion.

EXAMPLE VI

This example illustrates that the modified starch herein is as resistant to change during storage as gum arabic and more resistant than a starch based emulsifier which is presently used to emulsify flavor oils in beverages.

Enzyme-degraded OSA derivatives of waxy maize and of 50 WF acid-converted OSA waxy maize were prepared by the methods set forth in Example I. These starch compositions and controls which included gum arabic and an acid-converted OSA waxy maize that is currently used in beverage flavor oil emulsions were emulsified by the method described in Example V.

These emulsions were stored under refrigeration for 3 months. Brookfield viscosities were measured initially and after 3 months by the method set forth in Example II, except that a #5 spindle was used for viscosities from 1000–5000 cps. Visual observation of the enyzme degraded samples following 3 months under refrigeration showed good emulsion stability. Viscosity measurements are summarized in Table II.

TABLE II

| Emulsifier | Viscosity Changes in Flavor Oil Emulsions After Refrigerated Storage for 3 Months | |
|---|---|---|
| | Init. Viscosity (cps) | 3 Mo. Viscosity (cps) |
| Beta-Amylase-Degraded OSA Derivative of Acid Converted Waxy Maize | 1256 | 1576 |
| Beta-Amylase-Degraded OSA | 1520 | 1864 |

TABLE II-continued

| Emulsifier | Viscosity Changes in Flavor Oil Emulsions After Refrigerated Storage for 3 Months | |
| --- | --- | --- |
| | Init. Viscosity (cps) | 3 Mo. Viscosity (cps) |
| Derivative of Waxy Maize Beta-Amylase-Degraded OSA | 160 | 112 |
| Derivative of Waxy Maize Control: OSA Derivative of Acid-Converted Waxy Maize | 160 | 1880 |
| Control: Gum Arabic | 136 | 108 |

The results show that the emulsions prepared from beta-amylase-degraded starch compositions are as resistant as gum arabic emulsions to viscosity changes, gelling and oiling upon storage.

Thus, in aqueous dispersions and in emulsions the modified starches claimed herein display improved resistance to retrogradation and improved stability during storage over

EXAMPLE VII

This example illustrates that a modified starch of this invention may be prepared by reversing the sequence of steps which are set forth in Example I.

A 28% solids aqueous slurry of waxy maize starch was prepared, the pH was adjusted to 6.0-6.3 by the addition of 3% NaOH, and the slurry was jet-cooked at approximately 300° F. (149° C.) The cooked starch was placed in a constant temperature water bath and maintained at 55°-60° C. with constant stirring. The barley beta-amylase used in Example I was added to the cooked starch at a concentration of 1,650 DP° per 100 g dry basis of starch. The batch of beta-amylase used in this example contained 0.9 DU/ml of alpha-amylase activity. The degree of degradation was monitored by the funnel viscosity procedure set forth in Example I.

When the starch had reached a funnel viscosity of 30 seconds, the enzyme was deactivated by adding 10% HCl to for 30-60 minutes. After deactivation, the pH was adjusted to 7.0 by adding 3% NaOH.

The OSA derivative was prepared by thoroughly blending 3 g of octenylsuccinic acid anhydride per 100 g dry weight basis of starch into the neutralized, debranched starch dispersion. The reaction was permitted to continue at room temperature with good agitation for 4 hours.

A portion of this starch dispersion was spray-dried by the method set forth in Example I.

Orange oil emulsions were prepared as in Example V from a control starch that is commercially available for use as an emulsifier (an acid-converted OSA waxy maize derivative), and from the spray-dried and the aqueous dispersion samples of the debranched starch. The emulsions were subjected to at least eight freeze/thaw cycles, ranging from 1 to 10 days in length, and evaluated as in Example V.

The control starch formed an emulsion which was covered by a heavy slick of the orange oil after one freeze/thaw cycle. In contrast, the debranched starches formed emulsions which were stable through at least five freeze/thaw cycles. The spray-dried starch sample was stable through eight cycles. The aqueous starch dispersion sample showed a light orange oil slick beginning with the sixth cycle.

Thus, emulsions employing the modified starches of this invention, which have been prepared by enzymatic degradation of the starch, either before or after preparation of the starch derivative, display improved resistance to retrogradation and improved stability during storage over that of emulsions employing one of the commercial starch emulsifiers.

Now that the preferred embodiments of the present invention have been described in detail, various modifications and improvements thereon will become readily apparent to those skilled in the art. Accordingly, the scope and spirit of the invention are to be limited only by the claims and not by the foregoing specification.

I claim:

1. A modified starch having emulsification properties whose emulsions are characterized by improved stability and resistance to oiling and gelling during storage, comprising a starch derivative containing a hydrophobic group or both a hydrophilic group and a hydrophobic group, of which up to 70%, by weight, has been degraded by an exo-enzyme capable of cleaving 1,4-alpha-D-glucosidic linkages from non-reducing ends of the starch but incapable of cleaving 1,6-alpha-D-glucosidic linkages of the starch.

2. The modified starch of claim 1, wherein the starch is acid or heat-converted, or converted by alpha-amylase to a WF of up to about 60.

3. The modified starch of claim 1, wherein the exo-enzyme is beta-amylase.

4. The modified starch of claim 1, wherein the starch is a waxy maize starch.

5. The modified starch of claim 1, wherein the starch is gelatinized and has been derivatized by treatment with at least 0.25% of octenylsuccinic acid anhydride on a starch dry weight basis.

6. The modified starch of claim 5, wherein the starch is further derivatized to contain hydroxypropyl groups.

7. The modified starch of claim 1, wherein the starch derivative containing a hydrophobic group is gelatinized and the hydrophobic group comprises an alkyl, alkenyl, aralkyl or aralkenyl group containing at least five carbon atoms.

8. The modified starch of claim 1, wherein the starch derivative containing both a hydrophilic group and a hydrophobic group is gelatinized and contains a substituent radical having the following formula:

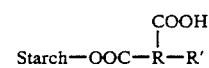

wherein R is a radical from the class of dimethylene and trimethylene radicals and R' is the hydrophobic group which comprises an alkyl, alkenyl, aralkyl or aralkenyl group containing at least five carbon atoms, and wherein the carboxyl radical COOH is the hydrophilic group.

9. A method for preparing a modified starch having emulsification properties whose emulsions are characterized by improved stability and resistance to oiling and gelling during storage, comprising the steps of (a) providing a gelatinized starch derivative, the derivative being characterized by each substituent radical containing a hydrophobic group or both a hydrophilic group and a hydrophobic group; and (b) degrading up to 70%, by weight, of the starch derivative to maltose with an exo-enzyme capable of cleaving the 1,4-alpha-D-glucosidic linkages from non-reducing ends of starch but incapable of cleaving 1,6-alpha-D-glucosidic linkages of starch.

10. The method of claim 9, wherein the starch is a waxy maize starch.

11. The method of claim 9, wherein the starch has been acid or heat-converted, or converted by alpha-amylase to a WF of up to about 60 prior to treatment with an exo-enzyme capable of cleaving the 1,4-alpha-D-glucosidic linkages from non-reducing ends of the starch but incapable of cleaving 1,6-alpha-D-glucosidic linkages of the starch.

12. The method of claim 9, wherein the starch has been derivatized by treatment with at least 0.25% of octenylsuccinic acid anhydride on a starch dry weight basis.

13. The method of claim 9, wherein the enzyme is beta-amylase and the enzyme degradation is carried out in aqueous dispersion containing up to 33% solids at an enzyme concentration from 334–1,110 degrees of diastatic power per 100 g of starch on a dry weight basis, and at a pH range between 3 and 10 and a temperature range from 20–75$C.

14. The method of claim 9, wherein the starch derivative contains a hydrophobic group, which hydrophobic group comprises an alkyl, alkenyl, aralkyl or aralkenyl group containing at least five carbon atoms.

15. The method of claim 9, wherein the starch derivative containing both a hydrophilic group and a hydrophobic group contains a substituent radical having the following formula:

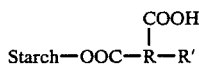

wherein R is a radical from the class of dimethylene and trimethylene radicals and R' is the substituent hydrophobic group which comprises an alkyl, alkenyl, aralkyl or aralkenyl group containing at least five carbon atoms, and wherein the carboxyl radical COOH is the hydrophilic group.

16. A method for preparing a modified starch having emulsification properties whose emulsions are characterized by improved stability and resistance to oiling and gelling during storage, comprising the steps of: (a) degrading up to 70%, by weight, of a gelatinized starch to maltose with an exo-enzyme capable of cleaving the 1,4-alpha-D-glucosidic linkages from non-reducing ends of starch but incapable of cleaving 1,6-alpha-D-glucosidic linkages of starch; and (b) reacting the enzymatically degraded starch with a reagent to provide a starch derivative containing a hydrophobic group or both a hydrophilic group and a hydrophobic group.

17. The method of claim 16, wherein the starch is a waxy maize starch.

18. The method of claim 16, wherein the starch has been acid or heat-converted, or converted by alpha-amylase to a WF of up to about 60 prior to treatment with an exo-enzyme capable of cleaving the 1,4-alpha-D-glucosidic linkages from non-reducing ends of starch but incapable of cleaving 1,6-alpha-D-glucosidic linkages of starch.

19. The method of claim 16, wherein the starch has been derivatized by treatment with at least 0.25% of octenylsuccinic acid anhydride on a starch dry weight basis.

20. The method of claim 18, wherein the enzyme is beta-amylase and the enzyme degradation is carried out in aqueous dispersion containing up to 33% solids at an enzyme concentration from 334–1,110 degrees of diastatic power per 100 g of starch on a dry weight basis, and at a pH range between 3 and 10 and a temperature range from 20°–75° C.

21. The method of claim 18, wherein the starch derivative contains a hydrophobic group, which hydrophobic group comprises an alkyl, alkenyl, aralkyl or aralkenyl group containing at least five carbon atoms.

22. The method of claim 18, wherein the starch derivative containing both a hydrophilic group and a hydrophobic group contains a substituent radical having the following formula:

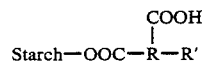

wherein R is a radical from the class of dimethylene and trimethylene radicals and R' is the substituent hydrophobic group which comprises an alkyl, alkenyl, aralkyl or aralkenyl group containing at least five carbon atoms, and wherein the carboxyl radical COOH is the hydrophilic group.

23. An emulsion for industrial applications containing the modified starch of claim 1.

24. An emulsion for industrial applications containing a modified starch prepared by the method of claim 9.

25. An emulsion for industrial applications containing a modified starch prepared by the method of claim 16.

* * * * *